United States Patent [19]
Meilus

[11] Patent Number: 5,810,875
[45] Date of Patent: Sep. 22, 1998

[54] LOW BACK AND HIP TREATMENT DEVICE

[76] Inventor: Algis A. Meilus, 331 N. Tessier Dr., St. Petersburg Beach, Fla. 33706

[21] Appl. No.: 854,633

[22] Filed: May 12, 1997

[51] Int. Cl.[6] ....................................................... A61F 5/00
[52] U.S. Cl. ............................................ 606/204; 606/237
[58] Field of Search ............................. 606/204, 237–245

[56] References Cited

U.S. PATENT DOCUMENTS

| | | | |
|---|---|---|---|
| 1,746,080 | 2/1930 | Hamilton | 606/237 |
| 4,090,517 | 5/1978 | Takenaka | 604/114 |
| 4,114,612 | 9/1978 | Benjamin | 128/76 R |
| 4,483,329 | 11/1984 | Shamos | 606/240 |
| 5,224,469 | 7/1993 | Mocny | 128/55 |

*Primary Examiner*—Michael Buiz
*Assistant Examiner*—David O. Reip
*Attorney, Agent, or Firm*—Dorothy S. Morse

[57] ABSTRACT

A muscular therapy treatment apparatus for patient self-treatment, and a method for its use, in applying concentrated pressure to deeply positioned non-palpable muscles underlying other muscle tissue in the hip area of a patient. The apparatus comprises a rigid planar base support and a treatment member upwardly depending from the central portion of the base support. The distal end of the treatment member has a sharp beveled edge for applying pressure to the deeply positioned muscles in a maximum range of sixty to one hundred pounds of pressure, or more, to lengthen them and thereby provide treated patients with relief from muscular tension and pain which had been a result of excess contraction in those muscles. In the preferred embodiment it is contemplated for the distal end of the treatment member to be removably attached so that sharp edges of differing widths and length can be used for different treatment needs.

14 Claims, 1 Drawing Sheet

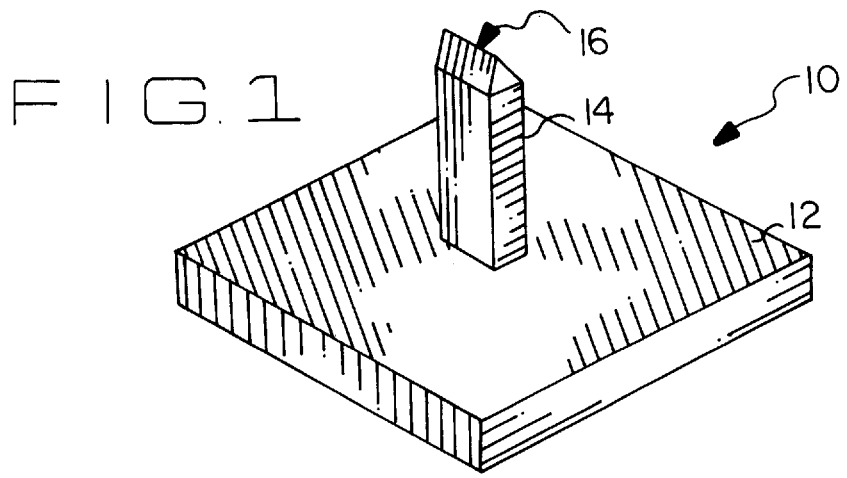
FIG. 1
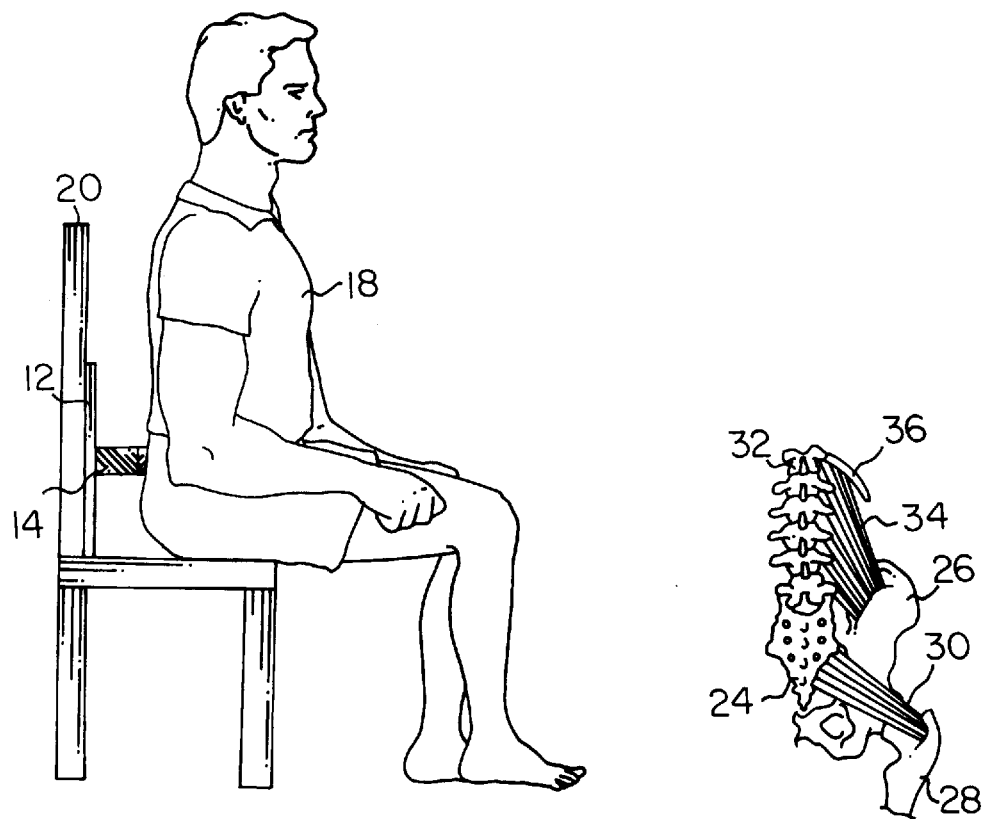
FIG. 2
FIG. 3

LOW BACK AND HIP TREATMENT DEVICE

BACKGROUND OF THE INVENTION

1. Field of the Invention

This invention relates to devices used for muscular therapy treatment of muscles in the hip area of a patient and which are associated with the lower portion of the spine, specifically to apparatus designed for patient self-treatment, and a method for its use, which has a planar base support with a treatment member upwardly depending therefrom, the treatment member having a sharp, beveled upper edge which can apply to deeply positioned non-palpable muscles underlying other muscle tissue, concentrated pressure in a maximum range of sixty to one hundred pounds of pressure, or more, to cause a lengthening of those of the deeply positioned muscles having excess contraction and thereby provide treated patients with relief from muscular tension and pain which had been a result of such excess contraction.

2. Description of the Prior Art

People commonly experience musculoskeletal pain and muscular tension, the source of which can be related to sports activities, other strenuous physical activity, accidents, poor posture, medical conditions, as well as other causes. Such pain is routinely treated by a variety of procedures which include the use of anti-inflammatory drugs, narcotic medications, thermal devices to raise or lower the temperature of affected tissues, electric stimulation, ultrasound, physical therapy, and massage therapy. However, while use of these treatment procedures can be effective for the temporary relief of adverse symptoms and limited mobility related thereto, they are usually not effective in relieving the cause of the symptoms. Also, the drugs and medications can induce adverse side effects in patients.

Muscular therapy is an alternative to the above-mentioned treatments in relieving musculoskeletal pain and tension. Unlike massage therapy which treats the muscle itself superficially, or physical therapy which works to strengthen weak spots, muscular therapy is the practice of repeatedly applying concentrated pressure to a muscle to release therefrom the build-up of lactic acid and other metabolic byproducts resulting from strenuous exercise, spasm, and/or tension. Upon such release, normal blood flow is restored to a muscle, diminishing pain and tension. As pressure is applied gradually and specifically to the point of spasm, sometimes the size of a small pea, three changes occur. First the muscle tissue lengthens, which is observable under a microscope. Second, the electrical activity of the nerve that innervates the area is reduced, a change which is measurable by EMG units, such as those typically used for biofeedback. Third, three acids are released, lactic acid, carbonic acid, and hyaluronic acid which result in the sting and discomfort felt by the patient during the application of the pressure. As this therapeutic process continues, the muscle tissues soften, the discomfort diminishes, and when all of the acid is removed from the muscle, one hundred pounds or more of pressure can usually be applied to the muscle with no discomfort.

Muscular therapy takes an engineering approach to treating the body by viewing it as a series of cables and fulcrums. By identifying the muscles operating different fulcrums during a repeated activity, diagnosis and treatment of pain and limited mobility caused by the repeated activity can be provided through the use of physics and the repetitive application of concentrated pressure to specific muscles one-at-a-time to lengthen them so that associated joints can move with less restriction. Relief provided by muscular therapy is often immediate and allows the quick resumption of activity. Preventative muscular therapy and self-treatment can prevent problems from recurring. Also, with continued muscular therapy, muscles have a faster response time, greater stamina, more leverage, and increased power and accuracy. Further, people with a skewed center of gravity, both disease-related and that due to poor posture, can achieve better balance through muscular therapy. In addition, repetitive application of pressure to injured tissue, in addition to relieving pain and enhancing blood circulation, desensitizes it and helps to speed the maturation of scars.

Traditionally, muscular therapy treatments have been performed manually by therapists using their fingers, hands, elbows, and the like, to press down on muscles to stretch them and enhance circulation therein. Muscular therapy is physically demanding on a therapist since in performing certain treatment procedures, such as when an attempt is made to loosen back muscles, the muscular therapist is required to apply pressures which sometimes exceed sixty pounds of pressure. As a work day progresses it is common for therapists to tire, and non-uniform treatments may result. Also as a consequence of the physical demands placed upon them, many muscular therapists have had to limit the amount of time they manually perform tissue manipulation. In muscular therapy applied to some parts of the body, patients can perform manual self-treatment with their hands, however, patients are prevented from effective self-treatment by hand manipulation of muscles in the side and rear portions of their hip area, due to the awkward angles required for a patient to reach such muscles and apply deep concentrated pressure thereto. The present invention provides a means for patient self-treatment of deeply positioned non-palpable muscles underlying other muscle tissue in a patient's hip area, such as the quadratus lumborum muscles attached between the transverse processes of the lumbar vertebrae and the crest of each ilium, as well as the piriformis muscles attached between the sacrum and the top portion of each femur, through the application of concentrated pressure which duplicates the type of pressure manually applied by muscular therapist hands. The present invention device does not tire during a day's work and will apply consistently uniform pressures. While it is known to have rounded devices with larger diameters, typically golf ball size, which can apply soothing, superficial pressure to such muscles, as well as devices which can stretch surface muscles in a patient's hip area, it is not known to have a treatment device which has a planar base support and a treatment member with a sharp beveled edge upwardly depending therefrom that can be used to apply deep concentrated pressure to muscles in a patient's hip area and wherein the application of deep concentrated pressure with the treatment device closely duplicates manual muscular therapy treatment procedures with muscular therapist hands, and further wherein the repeated amounts of deep, concentrated pressure being applied for periods of time approaching ten minutes causes muscles in the treated area, as well as muscles associated with the treated muscles, to lengthen and thereby provide the patient with relief from tension and pain which had been the result of excess contraction in those treated muscles.

The prior art thought to be most closely associated with the present invention are the inventions disclosed in U.S. Pat. No. 5,224,469 to Moeny (1993) and U.S. Pat. No. 4,114,612 to Benjamin (1978). The Moeny invention discloses a device which applies therapeutic pressure against the skin of a patient to compress tissues lying beneath the skin. It is contemplated for use in treating ailments responsive to accupressure therapy. The Moeny invention comprises a hand-held sensor which is electrically connected to means by which the amount of pressure applied can be measured. The Moeny invention differs from the present invention in that the Moeny invention has a blunt tip with which to contact a patient's skin and therefore it wouldn't be able to apply sufficient pressure to cause lengthening in the deeply positioned non-palpable muscles in the hip area of the patient, muscles such as the quadratus lumborum and the piriformis muscles which on an average human male are located approximately three to four inches below the skin surface. The action of the beveled sharp edge of the present invention creates concentrated pressure against a patient's skin of sufficient magnitude to reach and treat muscles positioned deeply beneath the skin. Also, the Moeny invention has no base support for its treatment member and therefore it must be hand-held against a patient's skin. As a result it would not reduce the physical demand placed upon the therapist, as does the present invention when the sharp upper edge of its treatment member is positioned between the patient and a patient support such as a chair, or when the patient lays in a supine position upon it, to apply deep concentrated pressure to the point of discomfort to deep muscles positioned between the transverse processes of the lumbar vertebrae and the crest of the ilium, as well as muscles between the sacrum and the top portion of the femur.

The Benjamin invention comprises a tension relieving device having three elongated members positioned between two triangular-shaped end caps. Each elongated member has a longitudinal arcuate free edge which projects at a 120° angle relative to the next adjacent elongated member. Thus, the Benjamin invention has three arcuate edges for tension-relieving muscular treatment, particularly in the occiput area at the base of the skull. However, the arcuate edges of the Benjamin invention would prevent it from treating deeply positioned non-palpable muscles in the area of a patient's hip to the point of discomfort, particularly those muscles positioned approximately three to four inches below the skin surface. Also, the present invention has an advantage over the Benjamin invention in that the present invention has a broader base support to more securely position the treatment member during use to apply concentrated pressures between sixty and one hundred pounds of pressure. Further, it is contemplated for the present invention to include an embodiment where the distal end of its treatment probe is removable so that beveled sharp edges of differing widths and length can be interchangeably employed for more versatile treatment of patients.

SUMMARY OF THE INVENTION

The primary object of the present invention is to provide a patient self-treatment device that duplicates the type of deep concentrated pressures applied manually by the hands of muscular therapists to non-palpable muscles deeply positioned in the hip area of a patient to reduce the physical burdens placed upon muscular therapists in applying the high pressures exceeding sixty pounds of pressure necessary to effectively treat such muscles to cause them to lengthen and thereby provide treated patients with relief from muscular tension and pain which had been the result on excess contraction in the treated muscles. It is also an object of the present invention to provide a device which can apply one hundred pounds of pressure, or more, to reach the quadratus lumborum and piriformis muscles which are located approximately three to four inches below the skin surface on an average human male. It is a further object of the present invention to provide a device which realigns the hip bones to relieve sciatica. A further object of the present invention is to provide a patient self-treatment device which duplicates manual muscular therapy treatments used in a patient's hip area, but provides more consistent and uniform patient treatments than human therapist hands which can become tired during the progress of a day's work. It is also an object of the present invention to provide a patient self-treatment device for duplication of manual muscular therapy treatments for the hip area that is made from materials which are low in cost, lightweight and thereby convenient to use, and easily cleaned between patient uses.

As described herein, properly manufactured and used, the present invention would provide a compact, easy-to-use treatment apparatus for applying deep concentrated pressure to muscles positioned in the lumbar area of a patient to relax and lengthen such muscles and thereby, as the muscles relax, permit more freedom of movement of the lumbar area, the hip bones, and the upper leg. It is important to note that the present invention does not apply force to bones to coax them into place in an effort to realign them. Any bone realignment resulting from muscular therapy treatment is a direct and automatic result of the elimination of excess muscle contraction. The present invention can be built from a variety of inexpensive materials and since it has a simple structure which is easy to manufacture, it could be made readily affordable to muscular therapists for widespread application, as well as for widespread self-treatment use by patients. Since it is a rigid device, it would not fatigue and could provide more consistent and more uniform treatments than the hands of a human muscular therapist. One preferred embodiment of the present invention contemplates its base support and treatment member to be made from plastic materials as a one piece unit through the use of molded construction. Thus the present invention would be light in weight and easy to clean between patient uses. The sharp beveled upper edge of the treatment member allows the treatment member to apply high, concentrated pressure to deeply positioned muscles which underlay other layers of muscle tissue, such as the quadratus lumborum muscles which are attached between the transverse processes of the lumbar vertebrae and the crest of each ilium, and the piriformis muscles which are attached between the sacrum and the tip of the great trochanter of the femur. By relaxing these muscles and properly realigning bones in the hip area, sciatica can be relieved. The present invention can be used by a patient lying on a flat surface with the intended treatment area positioned upon the sharp upper edge of the treatment member, or by a patient sitting in a chair with the present invention positioned between the patient and the back or side of the chair. When a patient is in a prone position with bent knees, depending upon the body weight of the patient, up to one hundred pounds of pressure, or more, can be applied to muscles deeply positioned within the patient's hip area. Known prior art devices distribute applied forces, instead of concentrating them, and are not able to reach and treat the deep muscles positioned in the hip area to lengthen them and provide a patient with increased mobility and relief from tension and pain. It is also contemplated for the distal end of the treatment member to be removably attached so that sharp edges of differing widths and length can be used for different treatment needs.

The description herein provides preferred embodiments of the present invention, but should not be construed as limiting the scope of the muscular therapy invention. For example, variations in the type of material from which the base support is made as long as the material is sufficiently rigid to perform its function and easily cleaned, the type of material from which the upwardly depending treatment member is made, the length of the treatment member, the thickness of the base support, and the process by which the base support and the treatment member are joined, other than those shown and described herein, can be incorporated into the present invention. Thus the scope of the present invention should be determined by the appended claims and their legal equivalents, rather than the examples given.

BRIEF DESCRIPTION OF THE DRAWINGS

FIG. 1 is a perspective view of the hip area muscular therapy treatment device having a planar base support and an upstanding treatment member with a sharp distal end.

FIG. 2 is a perspective view of the present invention being used between a patient and a patient supporting chair to treat muscles in the lumbar region of the patient's lower back.

FIG. 3 is a rear view of a patient's lumbar region with the piriformis muscle attached between the sacrum and the upper portion of the femur and the quadratus lumborum muscle attached between the 12$^{th}$ rib, transverse processes on spinal vertebrae, and the upper crest of the ilium of the hip bone with the present invention positioned adjacent to the quadratus lumborum muscle for treatment thereof.

DETAILED DESCRIPTION OF PREFERRED EMBODIMENTS

FIG. 1 shows a preferred embodiment of the present invention for treatment of muscles in the hip area of a patient and denoted by the reference number 10 as a whole. Hip muscle treatment device 10 comprises a rigid planar base support 12 and a treatment member 14 upwardly depending from the central portion of base support 12. The configuration and dimension of base support 12 is not critical to the present invention as long as it has sufficient dimension to hold treatment member 14 in a secure position during muscular therapy use. Also, the material from which base support 12 is made is not critical to the present invention as long as it has sufficient rigidity to support treatment member 14 while it applies adequate pressure to contracted muscles in the intended treatment area of a patient to lengthen them. In FIG. 1 base support 12 is shown to have a square configuration and in the preferred embodiment it is contemplated for each of the sides of base support 12 to have a minimum length of approximately six inches and for base support 12 and treatment member 14 to be made from plastic materials which are lightweight and easily cleaned after patient use. In the preferred embodiment it is also contemplated for base support 12 and treatment member 14 to be made as a single unit from molded construction. FIG. 1 also shows treatment member 14 having a distal end with a sharp edge 16. In hip muscle treatment device 10 it is contemplated for sharp edge 16 to have a beveled construction. Although not shown in FIG. 1, it is also contemplated for the distal end of treatment member 14, including sharp edge 16, to be releasably attached to the remainder of treatment probe 14 so that sharp beveled edges 16 of differing widths and length can be interchangeably used to treat differing patient needs.

FIG. 2 shows a patient 18 positioned upon a patient supporting chair 20, with base support 12 and attached treatment member 14 positioned between patient 18 and chair 20. FIG. 2 shows the distal end of treatment member 14 in contact with the lumbar area of patient 18. Although not shown, it is also contemplated for patient 18 to lie upon a flat surface with the present invention positioned between patient 18 and the flat surface and sharp edge 16 in contact with the hip area of patient 18. When patient 18 is in a prone position with bent knees, depending upon the body weight of patient 18, pressures at least exceeding sixty pounds of pressure, and sometimes pressures exceeding one hundred pounds of pressure, can be applied with treatment member 14 to muscles deeply positioned within the hip area of patient 18.

FIG. 3 shows the lumbar region of patient 18 having the piriformis muscle 30 attached between the sacrum 24 and the top portion of the femur 28. FIG. 3 also shows the quadratus lumborum muscle 34 attached between the 12$^{th}$ rib 36, the transverse processes of lumbar vertebrae 32, and the upper crest of the ilium of hip bone 26. Although not shown, in the average human male, the quadratus lumborum muscle 34 and the piriformis muscle 30 can be located between approximately three and four inches below the skin surface of patient 18. In the preferred embodiment it is contemplated for the height of treatment member 14 to range between approximately two-and-one-half inches and three-and-one-half inches.

To use the present invention, patient 18 would be placed upon a patient support, such as chair 20 or a flat surface such as a floor (not shown), with base support 12 in contact with the patient support and the distal end of treatment member 14 in contact with the intended treatment area in the lumbar region of patient 18. With patient 18 in proper position, sharp edge 16 will apply deep concentrated pressure to muscles in the treatment area of patient 18, such as the quadratus lumborum muscle 34 which is attached between the transverse processes of lumbar vertebrae 32 and the crest of the ilium of hip bone 26 or the piriformis muscle 30 which is attached between the sacrum 24 and the femur 28, to lengthen them for automatic realignment of hip bone 26 as a result of such lengthening, as well as elimination of pain previously associated with the treated area due to excess muscle contraction. Depending upon the body weight of patient 18, pressures at least exceeding sixty pounds of pressure, and sometimes pressures exceeding one hundred pounds of pressure, can be applied with treatment member 14 to muscles deeply positioned within the hip area of patient 18. It is contemplated for patient 18 to remain positioned against sharp edge 16 for periods of time not exceeding ten minutes. Relief of pain and increased mobility will often immediately follow muscular therapy treatment. Use of hip muscle treatment device 10 duplicates manual muscular therapy treatments performed by muscular therapist hands on deeply positioned, non-palpable hip muscles of patient 18 and thereby reduces the overall risk of muscular therapists to injury resulting from repeated application of over one hundred pounds of concentrated pressure to muscular tissues which is sometimes required to lengthen deeper muscles underlying other muscle tissue and located approximately between three and four inches below the skin surface of patient 18. Use of the present invention does not reduce the quality of treatment provided to patients, and it enables patients to administer uniform and effective self-treatment to muscles attached to their spinal vertebrae.

What is claimed is:

1. A device for applying concentrated pressure to muscles attached to the hip area of a patient, which simulates the type of deep concentrated pressure applied by muscular therapist hands to deeper non-palpable hip muscles to lengthen them for automatic hip bone alignment as a result of such lengthening, increased flexibility, and elimination of pain previously associated with the area treated as a result of excess muscle contraction, said device comprising:

a rigid planar base member having an upper surface; and a treatment member centrally connected to said upper surface, said treatment member upwardly depending from said upper surface and having attached thereon to a free end one of a plurality of removably attachable distal ends having a sharply angled edge, so that when said device is positioned between a patient and a patient supports movement of said patient against said sharply angled edge uniformly can apply deep concentrated pressure to lengthen deep non-palpable muscles attached in the hip area of the patient.

2. The device of claim 1 wherein each of said plurality of distal ends are provided with differing widths and length.

3. The device of claim 1 wherein said treatment member has a length dimension ranging between approximately two-and-one-half inches and three-and-one-half inches.

4. The device of claim 1 wherein said base support and said treatment member are made of materials sufficiently rigid to apply to deeply positioned non-palpable muscles pressures that exceed one hundred pounds of pressure.

5. The device of claim 1 wherein said base support and said treatment member are made as a one-piece unit with molded construction.

6. The device of claim 5 wherein said base support and said treatment member are made from lightweight plastic which can be easily cleaned between patient uses.

7. The device of claim 6 wherein said base support has a square dimension with each side being approximately six inches in length and wherein said treatment member has a length dimension ranging between approximately two-and-one-half inches and approximately three-and-one-half inches.

8. A method for applying concentrated pressure to deeply positioned non-palpable muscles attached to the hip area of a patient, pressure which simulates the type of concentrated pressure applied by muscular therapist hands to such muscles to lengthen them for automatic hip bone alignment as a result of such lengthening, increased flexibility, and elimination of pain associated with the area treated due to excess muscular contraction, said method the steps of:

providing a device comprising a rigid base member having an upper surface and a treatment member centrally attached to and upwardly depending from said upper surface, said treatment member having attached thereon to a free end one of a plurality of removably attachable distal ends having a sharply angled edge; and positioning said device between a patient and a patient support so that the sharply angled edge uniformly applies concentrated pressure to deeper muscles in the hip area of the patient as the patient moves the area against said edge.

9. The method of claim 8 further comprising providing the plurality of said distal ends with differing widths and length.

10. The method of claim 9 wherein said treatment member comprises a length dimension ranging between approximately two-and-one-half inches and three-and-one-half inches.

11. The method of claim 10 wherein said base member and said treatment member are made from materials sufficiently rigid so that they can apply pressures which exceed one hundred pounds of pressure to deeply positioned non-palpable muscles in the hip area of a patient.

12. The method of claim 11 wherein said base member and said treatment member are made as a one-piece unit with molded construction.

13. The method of claim 12 wherein said base member and said treatment member are made from lightweight plastic which can be easily cleaned between patient uses.

14. The method of claim 13 wherein said base member has a square perimeter dimension with each side being approximately six inches in length and said treatment member has a length dimension ranging between approximately two-and-one-half inches and approximately three-and-one-half inches.

* * * * *